United States Patent [19]

Chu

[11] Patent Number: 4,540,694

[45] Date of Patent: Sep. 10, 1985

[54] 1-PYRIDINE SUBSTITUTED QUINO-BENOXAZINES AND ANTIBACTERIAL USE

[75] Inventor: Daniel T. Chu, Vernon Hills, Ill.

[73] Assignee: Abbott Laboratories, North Chicago, Ill.

[21] Appl. No.: 604,198

[22] Filed: Apr. 26, 1984

[51] Int. Cl.³ ................. A61K 31/535; C07D 265/34
[52] U.S. Cl. ..................... 514/232; 514/233;
514/236; 514/99; 546/335; 546/342; 544/99
[58] Field of Search ........... 544/99; 424/248.52,
424/248.53, 248.55

[56] References Cited

U.S. PATENT DOCUMENTS

| 4,017,622 | 4/1977 | Minami et al. ............ 424/250 |
| 4,292,317 | 9/1981 | Pesson ..................... 424/250 |
| 4,382,892 | 5/1983 | Hayakawa et al. ........ 544/101 X |
| 4,443,447 | 4/1984 | Gerster et al. ............ 544/101 X |
| 4,473,568 | 9/1984 | Hutt ....................... 544/101 X |

FOREIGN PATENT DOCUMENTS

| 78362 | 5/1983 | European Pat. Off. . |
| 1147336 | 4/1969 | United Kingdom . |

OTHER PUBLICATIONS

Dauc, 84–043150/08, (1984), EP 101,829A.
Dauc, 84–039639/07, (1984), J59001489A.

*Primary Examiner*—Richard L. Raymond
*Attorney, Agent, or Firm*—Steven F. Weinstock; Martin L. Katz

[57] ABSTRACT

1-pyridine substituted quino-benoxazines having the formula:

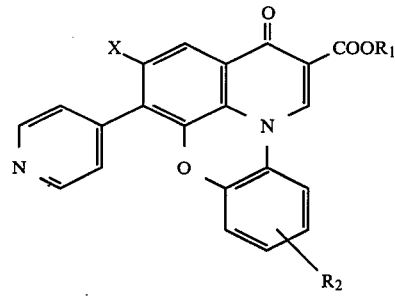

wherein X is halogen or hydrogen; $R_2$ is a substituent; and $R_1$ is hydrogen or a carboxy protecting group.

11 Claims, No Drawings

1-PYRIDINE SUBSTITUTED QUINO-BENOXAZINES AND ANTIBACTERIAL USE

This invention relates to new quino-benoxazine derivatives having antibacterial properties, compositions containing the new quino-benoxazine derivatives and methods of treating mammalian patients with the new quino-benoxazine derivatives.

It is known that certain quinoline compounds exhibit antibacterial properties, notably certain 7-piperazinyl-4-oxo-1,4-dihydroquinoline-3-carboxylic acids. In U.S. Pat. No. 4,017,622, there are disclosed certain 7-piperazinyl-4-oxo-1,4-dihydroquinoline-3-carboxylic acid derivatives which are substituted in the 1 position with an alkyl; benzyl or acetyl substituent. U.S. Pat. No. 4,292,317 discloses derivatives of 7-piperazinyl-4-oxo-1,4-dihydroquinoline-3-carboxylic acids wherein the 1 position is substituted by an alkyl group or a vinyl group. In U.S. Pat. No. 4,284,629, there are disclosed various 4-oxo-1,4-dihydroquinoline-3-carboxylic acids in which the 1 position is substituted with a cycloalkyl group.

This invention relates to novel antibacterial agents and, more particularly, to 1-(4-pyridyl)-4-oxo-4H-quino[2,3,4-i,j][1,4]benoxazine-5-carboxylic acids and derivatives having the formula:

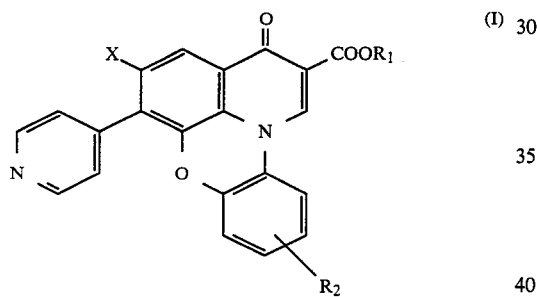

wherein X is a hydrogen or halogen, preferably fluoro, and $R_2$ is one or more of hydrogen, halogen, $C_1$ to $C_6$ alkyl including substituted derivatives thereof, nitro, carboxyl, cyano, methylenedioxy, a group having the formula —Y—$R_3$ wherein —Y— is —O— or —S— and $R_3$ is hydrogen or $C_1$ to $C_6$ alkyl, and an amine having the formula:

wherein $R_4$ and $R_5$ are each independently hydrogen or $C_1$ to $C_6$ alkyl.

$R_1$ is hydrogen or a carboxy-protecting group.

As used herein, the term "halogen" refers to chloro, bromo, fluoro and iodo groups, while the term "$C_1$ to $C_6$ alkyl" refers to loweralkyl groups including methyl, ethyl, propyl, isopropyl and butyl.

As indicated above, $R_2$ can be $C_1$ to $C_6$ alkyl as well as hydroxy and halo-substituted derivatives thereof. Such groups include a chloromethyl group, a chloroethyl group, a chloropropyl group, a hydroxyethyl group, and a trifluoromethyl group.

$R_2$ can also be a group of the formula —Y—$R_3$. Representative groups of this type include a hydroxy group, a mercapto group, a lower alkoxy group, such as methoxy, ethoxy, propoxy, as well as the thio analogs thereof, namely a methylmercapto group, and an ethylmercapto group.

As used herein, the term "carboxy-protecting group" refers to and includes the residue of a carboxylic acid ester group. Such carboxy-protecting groups are well known to those skilled in the art, having been extensively used in the protection of carboxyl groups in the penicillin and cephalosporin fields, as described in U.S. Pat. Nos. 3,840,556 and 3,719,667, the disclosures of which are incorporated herein by reference. In general, such carboxy-protecting groups can be relatively easily cleaved to yield the corresponding free carboxy group. Representative protecting groups include $C_1$—$C_8$ alkyl (e.g., methyl, ethyl, tertiary butyl), substituted alkyl (e.g., dimethylaminoethyl), benzyl and substituted derivatives thereof such as alkoxy and nitrobenzyl groups; also suitable are acyl groups such as pivaloyloxymethyl groups.

The preferred compounds of the present invention are those having the structure:

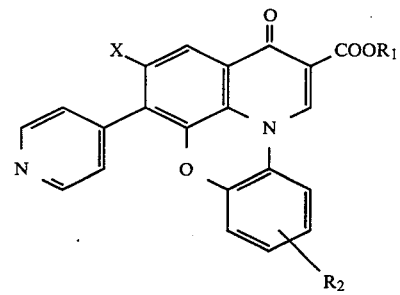

wherein X is fluoro, hydrogen and $R_1$ is as described above and $R_2$ is one or more of alkyl, halogen or methylenedioxy.

Representative of such preferred compounds are 1-(4-pyridyl)-4-oxo-quino[2,3,4-i,j][1,4]benoxazine-5-carboxylic acid, 1-(4-pyridyl)-10-fluoro-4-oxo-4H-quino[2,3,4-i,j][1,4]benoxazine-5-carboxylic acid, 1(4-pyridyl)-9,10-methylenedioxy-4-oxo-4H-quino[2,3,4-i,j][1,4]benoxazine-5-carboxylic acid, 1(4-pyridyl)-2-fluoro-4-oxo-4H-quino[2,3,4-i,j][1,4]-benoxazine-5-carboxylic acid, 1-(4-pyridyl)-2,10difluro-4-oxo-4H-quino[2,3,4-i,j][1,4]benoxazine5-carboxylic acid.

As will be appreciated by those skilled in the art, the pyridyl group in the 7-position can be substituted or unsubstituted. Suitable substituents on the pyridine ring include $C_1$ to $C_6$ alkyl, halogen, a group of the formula —Y—$R_3$ as described above, hydroxy and an amine of the formula:

wherein $R_{10}$ and $R_{11}$ are each independently selected from the group consisting of hydrogen, $C_1$ to $C_6$ alkyl, halo-substituted $C_1$ to $C_6$ alkyl and hydroxy-substituted $C_1$ to $C_6$ alkyl.

Also included within the scope of the present invention are pharmaceutically acceptable salts of the foregoing compounds. As used herein, the term "pharmaceutically acceptable salts" refers to nontoxic acid addition salts and alkaline earth metal salts of the compounds of Formula I. The salts can be prepared in situ during the final isolation and purification of the compounds of formula I, or separately by reacting the free base or acid functions with a suitable organic acid or base. Representative acid addition salts include the hydrochloride, hydrobromide, sulphate, bisulphate, acetate, oxalate, valerate, oleate, palmitate, stearate, laurate, borate, benzoate, lactate, phosphate, tosylate, mesylate, citrate, maleate, fumarate, succinate, tartrate, glucoheptonate, lactobionate, lauryl sulfate salts and the like. Representative alkali or alkaline earth metal salts include the sodium, calcium, potassium and magnesium salts. It has been found that the compounds of the present invention possess antibacterial activity against a wide spectrum of gram positive and gram negative bacteria, as well as enterobacteria. The compounds of the invention are therefore useful in the antibiotic treatment of susceptible bacterial infections in both humans and animals. In addition, the compounds, by reason of their in vitro activity, may be used in scrub solutions for surface inhibition of bacterial growth.

Susceptible organisms generally include those gram positive and gram negative, aerobic and anaerobic organisms whose growth can be inhibited by the compounds of the invention such as Staphylococcus, Lactobacillus, Streptococcus, Sarcina, Escherichia, Enterobacter, Klebsiella, Pseudomonas, Acinetobacter, Proteus, Citrobacter, Nisseria, Baccillus, Bacteroides, Peptococcus, Clostridium, Salmonella, Shigella, Serratia, Haemophilus, Brucella, and other organisms. In addition to exhibiting highly effective antibacterial activity, the compounds of the invention exhibit increased and improved solubility characteristics as compared with prior quinoline-3-carboxylic acid compounds in the art.

The compounds of Formula I may also be formulated into compositions together with pharmaceutically acceptable carriers for parenteral injection, for oral administration in solid or liquid form, for rectal administration, and the like.

Compositions according to the invention for parenteral injection may comprise pharmaceutically acceptable sterile aqueous or nonaqueous solutions, suspensions or emulsions. Examples of suitable nonaqueous carriers, diluents, solvents or vehicles include propylene glycol, polyethylene glycol, vegetable oils, such as olive oil, and injectable organic esters such as ethyl oleate. Such compositions may also contain adjuvants such as preserving, wetting, emulsifying, and dispersing agents. They may be sterilized, for example, by filtration through a bacteria-retaining filter, or by incorporating sterilizing agents into the compositions. They can also be manufactured in the form of sterile solid compositions which can be dissolved in sterile water, or some other sterile injectable medium immediately before use.

Solid dosage forms for oral administration include capsules, tablets, pills, powders and granules. In such solid dosage forms, the active compound is admixed with at least one inert diluent such as sucrose, lactose or starch. Such dosage forms can also comprise, as is normal practice, additional substances other than diluents, e.g., lubricating agents such as magnesium stearate. In the case of capsules, tablets and pills, the dosage forms may also comprise buffering agents. Tablets and pills can additionally be prepared with enteric coatings.

Liquid dosage forms for oral administration include pharmaceutically acceptable emulsions, solutions, suspensions, syrups and elixers containing inert diluents commonly used in the art, such as water. Besides such inert diluents, compositions can also include adjuvants, such as wetting agents, emulsifying and suspending agents, and sweetening, flavoring and perfuming agents.

Compositions for rectal administration are preferably suppositories which may contain, in addition to the active substance, excipients such as cocoa butter or a suppository wax.

Actual dosage levels of active ingredient in the compositions of the invention may be varied so as to obtain an amount of active ingredient effective to achieve antibacterial activity in accordance with the desired method of administration. The selected dosage level therefore depends upon the nature of the active compound administered, the route of administration, the desired duration of treatment and other factors. Generally, daily dosage levels of the compounds of Formula I of about 0.1 to about 750, more preferably about 0.25 to about 500 and most preferably about 0.5 to about 300 mg. of active ingredient per kg. of body weight are effective when administered orally to a mammalian patient suffering from an infection caused by a susceptible organism. If desired, the daily dose may be divided into multiple doses for administration, e.g., two to four times per day.

The compounds of Formula I may be prepared in accordance with the following reaction scheme:

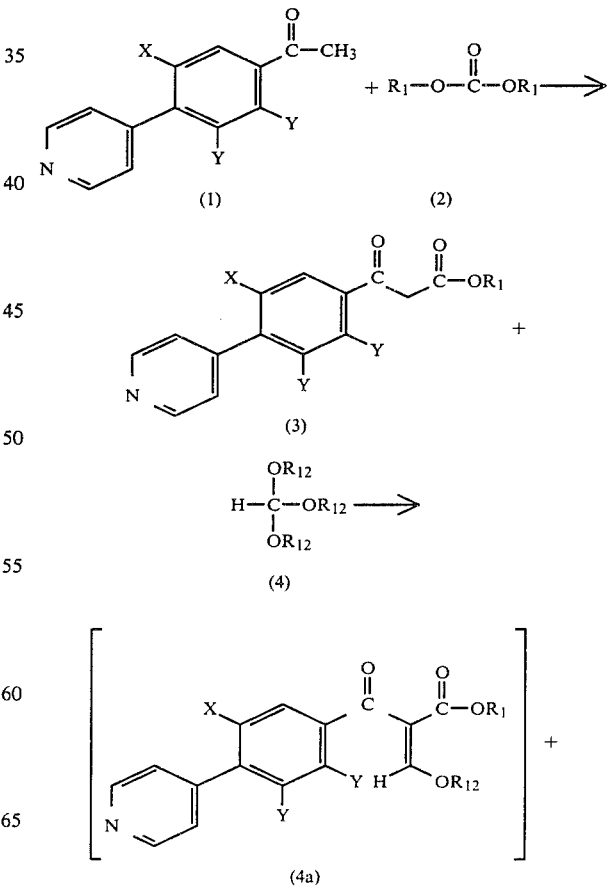

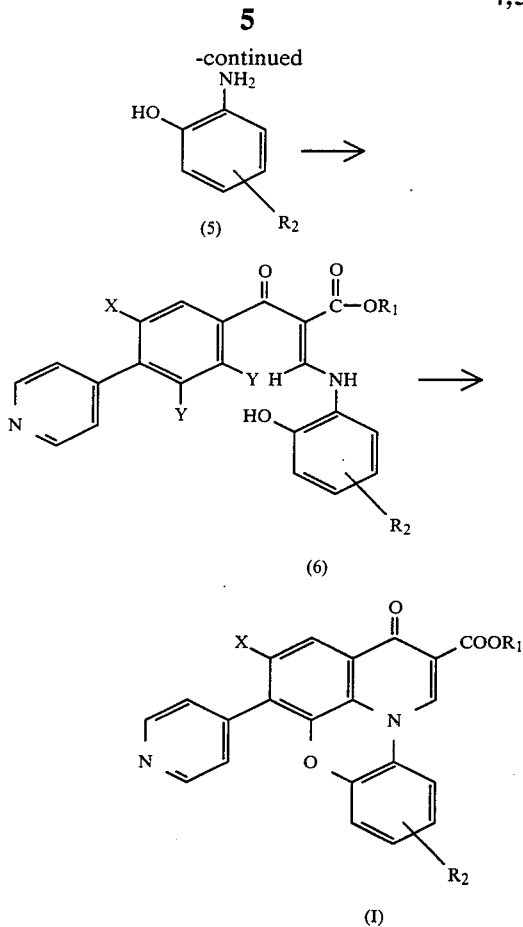

In accordance with the foregoing reaction scheme wherein Y is a halogen or a leaving group, the acetophenone (1) is reacted with a dialkoxycarbonate (2) in the presence of a strong base to obtain the corresponding β-ketoester (3). In the dialkoxycarbonate (2), $R_1$ may be an alkyl group of, for example, 1 to 10 carbon atoms, but is preferably loweralkyl, such as ethyl. Suitable bases include metal hydrides, such as sodium hydride, potassium hydride and the like, as well as metal alkoxides in alcohol, such as sodium ethoxide in ethanol. The preferred base is sodium hydride. Formation of the β-ketoester (3) is facilitated by reacting the acetophenone (1) with the dialkoxycarbonate (2) at elevated temperatures, such as from about 20° C. to about 120° C., and preferably from about 30° C. to about 90° C. until completion of the reaction. The β-ketoester may then be separated from the reaction mixture in a conventional manner.

The β-ketoester (3) is then treated with a trialkylorthoformate (4) in the presence of an acid anhydride, preferably acetic anhydride, followed by reaction with substituted or unsubstituted 2-hydroxyaniline (5) to obtain the enamino-ketoester (6). In the trialkylorthoformate (4), $R_{12}$ may be an alkyl group of, for example, from 1 to 10 carbon atoms, but is preferably loweralkyl, such as ethyl. Reaction with the trialkylorthoformate is preferably conducted at elevated temperatures, such as from about 50° C. to abut 150° C., and preferably from about 100° C. to about 140° C., to obtain an oily liquid, which may be isolated or unisolated, as desired (shown in brackets in the reaction scheme). Reaction of the latter with the substituted or unsubstituted 2-hydroxyaniline (5) is preferably conducted in an appropriate aprotic or non-aprotic solvent, preferably methylene chloride or tetrahydrofuran, and may be conducted at room or suitable elevated temperatures, as desired.

The enamino-ketoester (6) is then cyclized, such as by treatment with a strong base as defined above, preferably sodium hydride, to obtain the 1-(4-pyridyl)-4-oxo-4H-quino[2,3,4-i,j][1,4]benoxazine-5-carboxylic acid ester (I) ($R_1$=alkyl). Cyclization is conducted in the presence of an aprotic solvent, such as dimethoxyethane, dimethylformamide, tetrahydrofuran or chlorobenzene, and is preferably conducted at temperatures of about 20° C., to about 145° C., and more preferably at the reflux temperature of the solvent employed.

The ester (I) ($R_1$=alkyl) is subjected to hydrolysis such as by treatment with sodium hydroxide, or mineral acid, to form the free acid (I).

The 1-(4-pyridyl)-4-oxo-4H-quino[2,3,4-i,j]-[1,4-]benoxazine-5-carboxylic acid (I) ($R_1$=H) can be converted into the corresponding ester, if desired, by conventional esterification procedures, such as by treating the free acid (I) with the appropriate alcohol in the presence of an acid catalyst, by converting the free acid (I) into the corresponding acid chloride followed by displacement of the chloro radical with the appropriate alcohol, or by treating the sodium salt of the acid (I) with a suitable reactive halide, such as chloromethylpivalate in dimethoxyethane to obtain, for example, the pivaloyloxymethyl ester.

The foregoing may be better understood from the following examples, which are presented for purposes of illustration and are not intended to limit the scope of the inventive concepts. As used in the following examples, the references to compounds, such as (1), (2), (3), etc., and to substituents, such as $R_1$, $R_2$, etc., refer to the corresponding compounds and substituents in the foregoing reaction scheme and in formula I.

EXAMPLE 1

1-(4-pyridyl)-2-fluoro-4-oxo-4H-quino[2,3,4-i,j][1,4]benoxazine-5-carboxylic acid (a) A cold solution of 28.4 g. 2,3-dichloro-4-(pyridyl)-5-fluoroacetophenone in 350 ml. diethylcarbonate is slowly added to 8.0 g. 60% sodium hydride-in-oil suspension. The mixture is heated at 80° C. for 3 hours, then poured into 700 ml. ice cold water solution containing 25 ml. acetic acid. The mixture is extracted with three 400 ml. portions of ether. The organic phase is dried over MgSO₄, evaporated and the obtained oil is purified through silica gel column to give pure (3). (Y=Cl, $R_1$=C₂H₅, X=F).

(b) A solution of 16.6 g. of β-ketoester (3) ($R_1$=C₂H₅, Y=Cl, X=F) in 14 ml. of triethylorthoformate and 35 ml. of acetic anhydride is heated at 135° C. for 1-½hours with the removal of the ethyl acetate formed during the reaction. The solution is evaporated under reduced pressure to a mobile oil. The oil is then dissolved in 150 ml. of methylene chloride and 7.5 g. of 2-hydroxyaniline is added into the solution. After 1 hour, the solution is evaporated to dryness yielding (6), wherein $R_1$=C₂H₅, Y=Cl, $R_2$=H, X=F.

(c) To a cold solution of 14 g. of the preceding product (6) ($R_1$=C₂H₅, $R_2$=H, Y=Cl, X=F), in 140 ml. tetrahydrofuran (THF) is slowly added 2.5 g. of a 60% sodium hydride-in-oil suspension. The mixture is refluxed for 6 hours and is cooled and diluted with water to a volume of 1.5 liters. The mixture is then filtered and the solid is washed with 1:1 hexane/ether solution to obtain (I) wherein $R_1=C_2H_5$, $X=F$, $R_2=H$). (d) To a suspension of 5 g. of (I) ($R_1=C_2H_5$, $X=F$, $R_2=H$) in 30 ml. of THF is added a sodium hydroxide solution (0.63 g. in 10 ml. water). The mixture is heated at 80° C. for 2 hours resulting in a clear solution which is evaporated under reduced pressure to dryness. The solid is dissolved in 200 ml. water, and 2 ml. acetic acid is added. The resulting precipitate is filtered and washed with cold water, to produce 1-(4-pyridyl)-2-fluoro-4-oxo-4H-quino-[2,3,4-i,j][1,4]benoxazine-5-carboxylic acid (I) ($R_1=H$, $R_2=H$, $X=F$).

EXAMPLE 2

1-(4-pyridyl)-2,10-difluoro-4-oxo-4H-quino[2,3,4-i,j][1,4]benoxazine-5-carboxylic acid The procedure of Example 1 can be repeated replacing 2-hydroxyaniline with 2-hydroxy-4-fluoroaniline in Example 1(b) to obtain 1-(4-pyridyl)-2,10-difluro-4-oxo-4H-quino[2,3,4-i,j][1,4]benoxazine-5-carboxlic acid (I), ($R_1=H$, $R_2=10$-fluoro, $X=F$).

EXAMPLE 3

In the described fashion as Example 1 replacing 2-hydroxyaniline in Example 1(b) with 2,4-dihydroxyaniline, one can obtain 1-(4-pyridyl)-2-fluoro-10-hydroxy-4-oxo-4H-quino[2,3,4-i,j][1,4]benoxazine-5-carboxylic acid (I) ($R_1=H$, $R_2=10$-hydroxy, $X=F$).

EXAMPLE 4

The procedure of Example 1 can be repeated replacing 2-hydroxyaniline in Example 1(b) with 2-hydroxy-4-methoxyaniline to obtain 1-(4-pyridyl)-2-fluro-10-methoxy-4-oxo-4H-quino[2,3,4-i,j][1,4]benoxazine-5-carboxylic acid (I), ($R_1=H$, $R_2=10$-methoxy, $X=F$).

EXAMPLE 5

In the described fashion as Example 1 replacing 2-hydroxyaniline in Example 1(b) with various substituted 2-hydroxyaniline, one can obtain additional substituted 1-(4-pyridyl)-2-fluoro-4-oxo-4H-quino[2,3,4-i,j][1,4]benoxazine-5-carboxylic acid (I) as summarized in Table I.

TABLE I

| 2-Hydroxyaniline Replacement | Compound I obtained ($X = F$, $R_1 = H$) |
|---|---|
| R =  | R = |
| (a) 6-fluoro | 8-fluoro |
| (b) 5-fluoro | 9-fluoro |
| (c) 3-fluoro | 11-fluoro |
| (d) 4,6-difluoro | 8,10-difluoro |
| (e) 4-chloro | 10-chloro |
| (f) 4-methyl | 10-methyl |
| (g) 4,5-methylenedioxy | 9,10-methylenedioxy |

EXAMPLE 6

In the described fashion as Example 1 replacing 2,3-dichloro-4-(4-pyridyl)-5-fluoroacetophenone in Example 1(a) with 2,3-dichloro-4-(4-pyridyl)acetophenone and optionally, 2-hydroxyaniline in Example 1(b) with 2-hydroxy-4-fluoroaniline or 2-hydroxy-4,5-methylenedioxyaniline, one can obtain the following three compounds:

(a) 1-(4-pyridyl)-4-oxo-4H-quino[2,3,4-i,j][1,4]benoxazine-5-carboxylic acid (I) ($R_1=H$, $X=H$, $R_2=H$).

(b) 1-(4-pyridyl)-10-fluoro-4-oxo-4H-quino[2,3,4-i,j][1,4]benoxazine-5-carboxylic acid (I) ($R_1=H$, $X=H$, $R_2=10$-fluoro).

(c) 1-(4-pyridyl)-9,10-methylenedioxy-4-oxo-4H-quino[2,3,4-i,j][1,4]benoxazine-5-carboxylic acid (I) ($R_1=H$, $X=H$, $R_2=9,10$-methylenedioxy).

It will be understood that various changes and modifications can be made in the details of formulation, procedure and use without departing from the spirit of the invention, especially as defined in the following claims.

What is claimed is:

1. A compound having the formula:

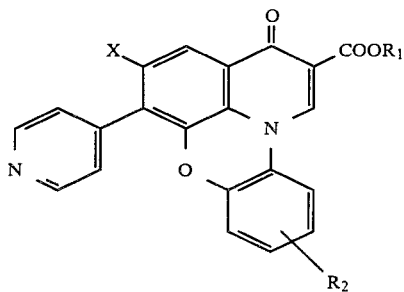

wherein $R_1$ is hydrogen or a carboxy protecting group; x is halogen or hydrogen; $R_2$ is one or more groups seclected from the group consisting of hydrogen, halogen, methylenedioxy, $C_1$ to $C_6$ alkyl, halo-substituted $C_1$ to $C_6$ alkyl, hydroxy-substituted $C_1$ to $C_6$ alkyl, a group having the formula:

$$-Y-R_3$$

wherein $-Y-$ is $-O-$ or $-S-$ and $R_3$ is hydrogen of $C_1$ to $C_6$ alkyl, and an amine group having the formula:

wherein $R_4$ and $R_5$ are independently hydrogen or $C_1$ to $C_6$ alkyl, wherein the 1-(4pyridyl) group is optionally substituted with one or more substituents independently selected from the group consisting of hydrogen, $C_1$ to $C_6$ alkyl, halogen, hydroxy, a group of the formula $-Y-R_3$ and an amine of the formula:

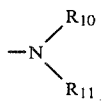

wherein $R_{10}$ and $R_{11}$ are independently selected from the group consisting of hydrogen, $C_1$ to $C_6$ alkyl, halo-substituted C to $C_6$ alkyl and hydroxy-substituted $C_1$ to $C_6$ alkyl, and pharmaceutically acceptable salts thereof.

2. A compound as defined in claim 1 wherein $R_1$ is hydrogen.

3. A compound as defined in claim 1 wherein $R_2$ is hydrogen, $R_1$ is hydrogen, and X is fluoro.

4. A compound as defined in claim 1 wherein $R_2$ is fluoro, $R_1$ is hydrogen and X is hydrogen.

5. A compound as defined in claim 1 wherein $R_2$ is fluoro, $R_1$ is hydrogen and X is fluoro.

6. A compound as defined in claim 1 wherein $R_2$ is difluoro, $R_1$ is hydrogen, and X is fluoro.

7. A compound as defined in claim 1 wherein $R_2$ is methylenedioxy, $R_1$ is hydrogen and X is hydrogen.

8. A compound as defined in claim 1 wherein $R_2$ is methylenedioxy, $R_1$ is hydrogen and X if fluoro.

9. A compound as defined in claim 1 wherein the 1-(4-pyridyl) group is unsubstituted.

10. A composition having antibacterial activity in pharmaceutical dosage form containing a diluent and a compound as defined in claim 1.

11. A method of treating a bacterial infection in a patient comprising administering to a patient in need of such treatment a therapeutically effective amount of a compound as defined in claim 1.

* * * * *